United States Patent
Kinser et al.

(10) Patent No.: US 10,067,061 B2
(45) Date of Patent: Sep. 4, 2018

(54) PATCH CLAMP TECHNIQUE WITH COMPLEMENTARY RAMAN SPECTROSCOPY

(71) Applicant: International Business Machines Corporation, Armonk, NY (US)

(72) Inventors: Emily R. Kinser, Poughkeepsie, NY (US); Roy R. Yu, Poughkeepsie, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/858,472

(22) Filed: Dec. 29, 2017

(65) Prior Publication Data

US 2018/0143140 A1    May 24, 2018

Related U.S. Application Data

(63) Continuation of application No. 15/177,829, filed on Jun. 9, 2016.

(51) Int. Cl.
    *G01J 3/44*            (2006.01)
    *G01N 21/65*          (2006.01)
    *G01J 3/18*            (2006.01)
    *G01J 3/02*            (2006.01)

(52) U.S. Cl.
    CPC .............. *G01N 21/658* (2013.01); *G01J 3/02* (2013.01); *G01J 3/18* (2013.01); *G01J 3/44* (2013.01); *G01N 21/65* (2013.01)

(58) Field of Classification Search
    CPC ................. G01N 21/65; G01N 21/658; G01N 2021/656; G01J 3/02; G01J 3/44
    See application file for complete search history.

(56) References Cited

U.S. PATENT DOCUMENTS

2015/0044751 A1\*    2/2015    Chiou ................... C12M 35/02
                                                            435/173.6

\* cited by examiner

*Primary Examiner* — Abdullahi Nur
(74) *Attorney, Agent, or Firm* — Louis J. Percello; Otterstedt, Ellenbogen & Kammer, LLP

(57) ABSTRACT

Surface enhanced Raman spectroscopy is employed to obtain chemical data with respect to cells while electrophysiological data relating to cell membranes is obtained using the patch clamp technique. A SERS-facilitating assembly is coupled to a micropipette and is used in conjunction with a monochromatic light source for generating scattered light. Surface enhanced Raman spectroscopy is employed to obtain the chemical data. Electrophysiological data is obtained using the same micropipette to perform the patch clamp technique.

17 Claims, 6 Drawing Sheets

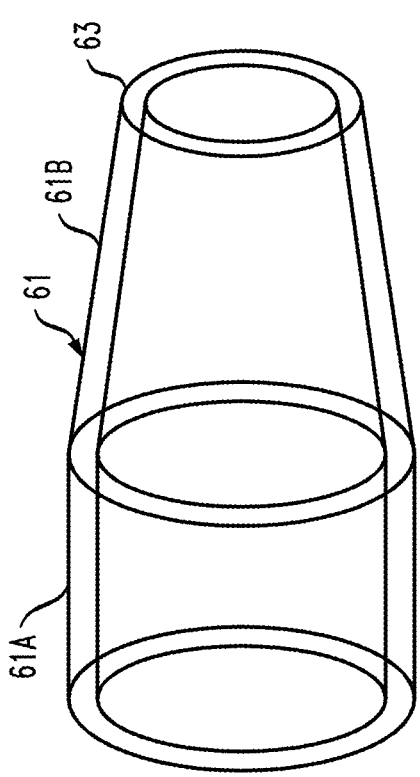
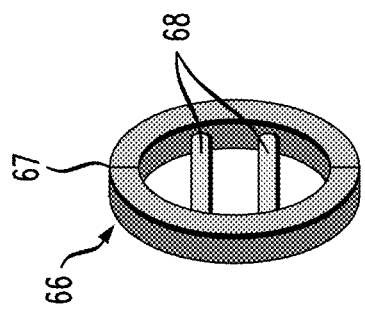
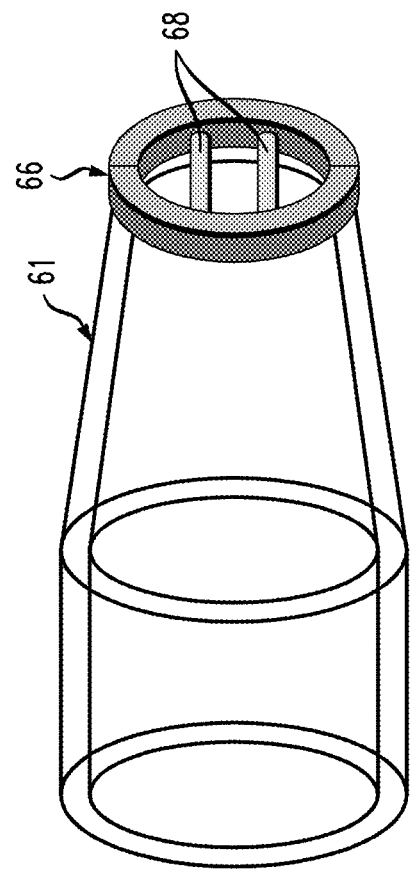

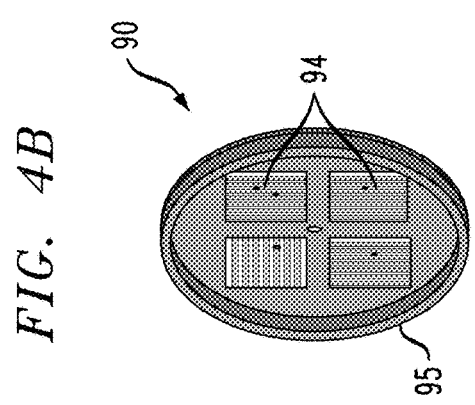
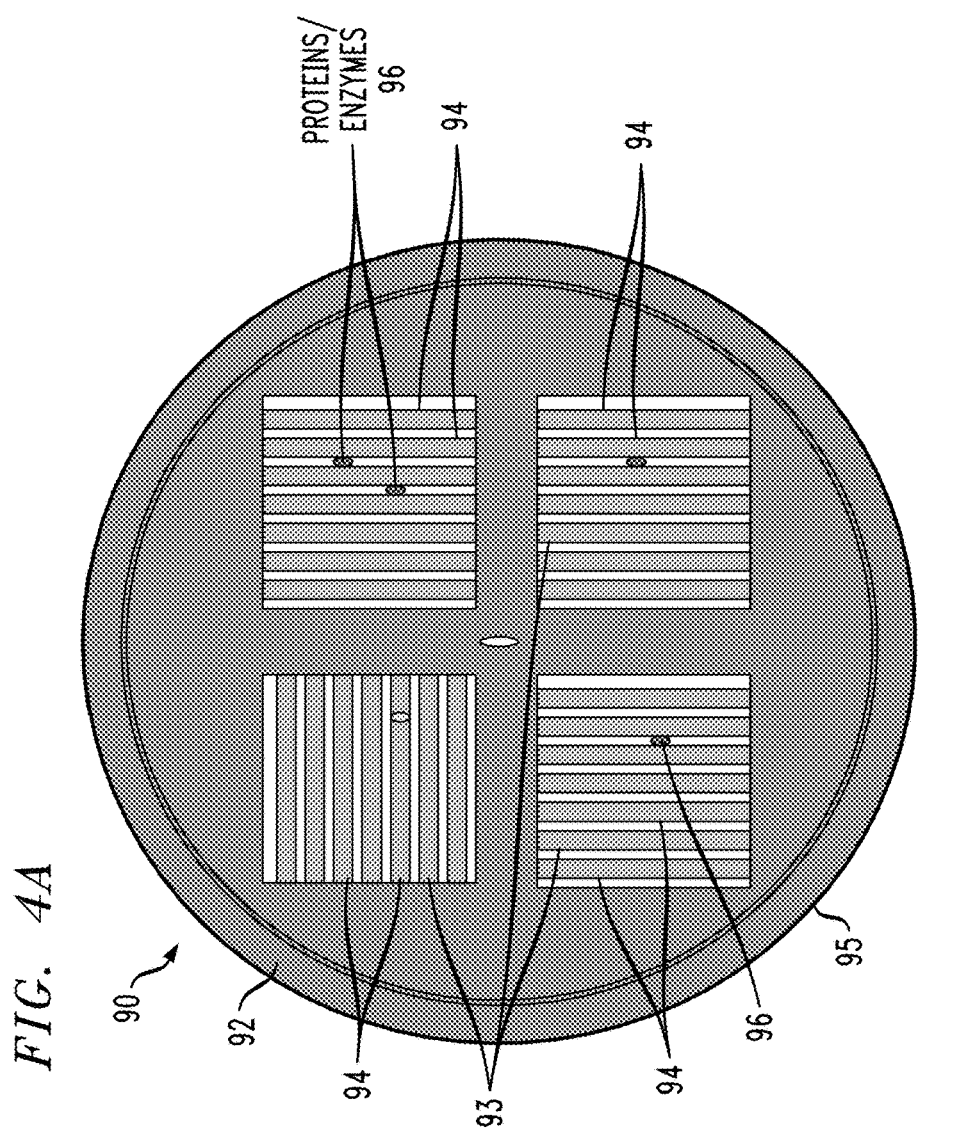

PATCH CLAMP TECHNIQUE WITH COMPLEMENTARY RAMAN SPECTROSCOPY

CROSS REFERENCE TO RELATED APPLICATION

This patent application is a continuation of U.S. patent application Ser. No. 15/177,829 filed Jun. 9, 2016 and entitled PATCH CLAMP TECHNIQUE WITH COMPLEMENTARY RAMAN SPECTROSCOPY, the disclosure of which are expressly incorporated herein by reference in its entirety.

The present disclosure relates generally to processes and assemblies for obtaining electrophysiological and chemical information using the patch clamp technique and complementary surface enhanced Raman and surface enhanced Terahertz-Raman spectroscopy.

BACKGROUND

Electromagnetic radiation spectrum covers a wide wavelength range, from gamma-ray, x-ray, UV, visible light, infra-red (near and far IR), terahertz (THz), to microwave and radio wave. The energy levels in the IR (10 THz to 400 THz) and THz (0.1-10 THz) regions coincide with molecular bond vibrational and rotational energies. Therefore, in science and technology the IR and Terahertz regions of the radiation spectrum are typically used for chemical and molecular structure identification. Each chemical and biological molecule and macromolecule (protein, enzyme) has its molecular vibrational and rotational energy signatures, unique finger prints to the species, detectable and identifiable in the IR and THz spectrum region.

IR spectroscopy is widely used for chemical analysis. IR spectroscopy typically uses a "white" light (a broad band with all wave lengths included) to illuminate the sample and detect the missing (absorbed) components in the spectrum, such implicating the presence of specific vibrational chemical bonds and, therefore the presence of the chemical species. These vibrational bonds can also be probed using a single wavelength laser to detect the spectrum of the scattered laser energy (called Raman scattering, or Raman spectroscopy). With the advancement of solid state lasers, such as quantum cascade lasers, and optical filters, Raman spectroscopy has become the favored technique in micro and nano scale chemical and structural analysis, due to the accuracy and stability of modern microelectronics and optics.

Raman spectroscopy typically involves the illumination of a sample with a laser beam (with a well-defined wave length and tight half-width) and collecting the radiation scattered by the illuminated sample for analysis. LabRAM® ARAMIS from Horiba Scientific is one of such instrument with microscope and stepping function. Once illuminated by the laser the electrons in the molecules in the sample can become excited and either absorb or lose a photon. When the excited molecule returns to its ground state it will emit a photon (light) with the energy unique to the structure of the emitting molecule. If a molecule absorbs a photon and reemits, it's called Stoke's emission, otherwise, anti-Stoke's emission. With the aid of a well-focused laser Raman spectra can be obtained from small volumes and allow the identification of species present in the volumes.

Terahertz spectra lay between IR and microwave in the electromagnetic spectrum. In technology, the Terahertz (sometime called mm wave) region is also termed "Terahertz gap". This is because there is almost no natural occurring radiation source for terahertz. IR radiation is produced by photon excitation which is best for >10 THz while microwave radiation by electron excitation good for <0.1 THz. Due to the difference in source and detection, THz spectroscopy is typically a different method from Raman spectroscopy which uses IR. Recently, however, a detection method has been developed by Ondax, Inc. which, using a volumetric filter, can combine Raman and THz in a single system. Low energy phonons can also be detected using a BragGrate™ Notch Filter from OptiGrate Corp., for example, in volumetric holographic grating.

Biological molecules and macromolecules (protein/enzyme) are typically very large molecules, containing thousands and millions of H, C, O, N, and other atoms with a well-defined and folded structure. Such large molecules not only exhibit molecular bond vibration, they also have collective motions (rotation, shear, breath, torsion). For a C—H bond, the vibrational energy is typically between 2700-3300 (l/cm) (or 80-100 THz) depending on the type of the molecule the bond resides. For C—C bond, the bond energy range (1200-1700 l/cm), (or 40-50 THz) also depending on the bond's environment. Typically, the heavier an atom the lower the vibrational energy, with all other factors being equal. IR Raman spectroscopy covers a range of 333-5000 l/cm. (10-150 THz). Energy below 333 l/cm (0.1 to 10 THz) belong to Terahertz domain. For very large molecules such as macromolecules, additional vibrational collective modes occur. These collective motions have energy levels low in the terahertz region (<333 l/cm, or <10 THz). Increasingly, THz spectroscopy in conjunction with Raman spectroscopy are used for protein and macromolecule structural analysis.

Extending Raman into the terahertz region for macromolecule (very large proteins and enzymes) structure detection, such as protein structural vibration in membrane is a new development. Currently, there is no viable method to effectively excite and detect such motion (in-vivo in membrane). Proteins and enzymes (such as lysozyme and ribosome) are very large molecules and can have their crystal structure determined by x-ray crystallography. But there is no viable method to determine their structure while they are in-vivo (in membrane). There is no direct link between their DNA/ amino sequence and their enzymatic functionality. Terahertz-Raman allows for the first time for such determination. In a normal terahertz, the wave length is such that terahertz cannot focus onto a single molecule. A normal SERS Raman can detect single molecule chemically but not its macrostructure. Terahertz-Raman is to use very high resolution Raman to obtain terahertz information (molecular structure through its acoustic signature).

Raman spectroscopy (333-5000 l/cm) can be employed to detect the presence of biological and medical specimens, including organic molecules such as proteins, glucose, and insulin most efficiently in powder and in crystalline form. Raman is also used as light scattered in solution by analyte molecules is unique to the particular molecules, which allows the determination of the molecules that are present within solvent, tissue, or blood samples. For in-situ, in-vitro, and in-vivo analysis, surface enhanced Raman spectroscopy (SERS) can be used. Surface-enhanced Raman spectroscopy (SERS) is a technique that enhances Raman scattering by molecules interacting with rough metal surfaces or nanostructures. The enhancement mechanism relates to laser stimulated surface plasmon resonance in certain metals, Au, Ag, Pt, being most common. When the incident laser frequency coincides with the surface plasmon, strong absorption and reemission of the laser energy occurs, and so too the signals from the molecules present on such surfaces. Surface plasmon resonance has been widely used in bio-sensors for biomolecule antigens detection without the use of labeling agents. Advancements in nanotechnology have allowed nanoparticles suspended in solution and mixed with the chemical to be analyzed. The presence of the nanoparticles in the vicinity of such chemicals greatly enhances Raman detectability. It is, however, difficult to introduce suspended particles in vivo. Biomolecules such as proteins have been detected using SERS substrates. Nanopatterned bulk metallic glass (BMG) such as Pt-BMG can enhance glucose detection. The enhancement of signals obtained using SERS technology may include different modes from those obtained using traditional non-enhancing techniques as the symmetries of detected molecules can be changed, depending on the polarity of the laser.

The patch clamp technique is employed in the study of ion channels in cells. The technique generally involves the use of a micropipette in contact with a patch of cell membrane, for example a neuron membrane. A glass micropipette having a tip diameter of about one to ten microns and filled with a suitable electrolyte solution encloses an area of a membrane surface (a "patch") that contains one or more ion channels. Suction may be applied to form a high-resistance seal that electrically isolates the membrane patch for "cell-attached" recording or, in some cases, to rupture the membrane for "whole-cell" recording. The micropipette is retracted following membrane contact in some variations of the patch clamp technique, namely for "inside-out" and "outside-in" recording, in order to separate the patch from the cell membrane. The various techniques allow the recording of electrical currents from a small patch or a whole cell. Micropipettes having relatively large diameters, for example 10-25 μm, have been employed for forming gigaseals in the study of electrogenic pump and exchange transport.

SUMMARY

Principles of the present disclosure provide techniques and devices for obtaining real time chemical information using Raman spectroscopy in conjunction with obtaining electrophysiological data using the patch clamp technique.

In accordance with a first exemplary embodiment, an exemplary method includes obtaining a micropipette including an open tip portion configured for facilitating surface enhanced Raman spectroscopy and positioning the tip portion of the micropipette in adjoining relation to a cell membrane. An electrolyte solution is introduced within the micropipette. Suction is applied through the micropipette while the tip portion is in adjoining relation to the cell membrane. The method further includes conducting a patch clamp technique using the micropipette to obtain electrophysiological data with respect to the cell membrane, causing monochromatic light having a selected wavelength to be directed towards the tip portion of the micropipette, and conveying surface enhanced Raman scattered light generated at the tip portion of the micropipette to a detector for spectral analysis of the scattered light.

An exemplary assembly for performing the patch clamp technique as well as facilitating chemical sensing includes a micropipette having a body portion and a tip portion. A SERS-facilitating assembly is attached to the tip portion of the micropipette and includes an annular surface for providing sealing contact with a cell membrane during performance of the patch clamp technique. The SERS-facilitating assembly is configured for interacting with selected molecule(s) and thereby enhancing Raman scattering while allowing fluid passage therethrough.

A further exemplary method includes obtaining a micropipette having an open end portion and obtaining a SERS-facilitating assembly including a base, an opening extending through the base, and a plurality of nano-rods attached to the base. The nano-rods extend across the opening. The method further includes attaching the SERS-facilitating assembly to the open end portion of the micropipette.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed.

Substantial beneficial technical effects are provided. For example, one or more embodiments may provide one or more of the following advantages:

Trace chemical sensing;
Obtaining electric properties relating to cell membrane ion channels;
Real time correlation of chemical and electrical data relating to ionic channels;
Surface-enhanced Raman spectroscopy;
Single molecule detection using SERS (including Raman spectroscopy extended into the terahertz region).

These and other features and advantages will become apparent from the following detailed description of illustrative embodiments thereof, which is to be read in connection with the accompanying drawings.

BRIEF DESCRIPTION OF THE DRAWINGS

The following detailed description, given by way of example, will best be appreciated in conjunction with the accompanying drawings, in which:

FIGS. 3A-3C include a flow diagram showing fabrication of the exemplary micropipette assembly;

FIG. 4A is a schematic, top plan view of an exemplary nanorod assembly for facilitating surface-enhanced Raman spectroscopy;

FIG. 4B is a perspective view thereof;

DETAILED DESCRIPTION

Principles of the present disclosure will be described herein in the context of illustrative embodiments. It is to be appreciated, however, that the specific embodiments and/or methods illustratively shown and described herein are to be considered exemplary as opposed to limiting. Moreover, it will become apparent to those skilled in the art given the teachings herein that numerous modifications can be made to the embodiments shown that are within the scope of the claims. That is, no limitations with respect to the embodiments shown and described herein are intended or should be inferred.

The assemblies and techniques disclose herein may be used to facilitate, inter alia, single molecule detection using SERS Raman and SERS Terahertz-Raman technology, for the application of in-vivo membrane proteins chemical and structure detection. Terahertz-Raman with surface enhancement as disclosed herein allows single molecule Terahertz information (large molecular structural information) to be detected and the linking of such information to their enzymatic function.

Figure 1:
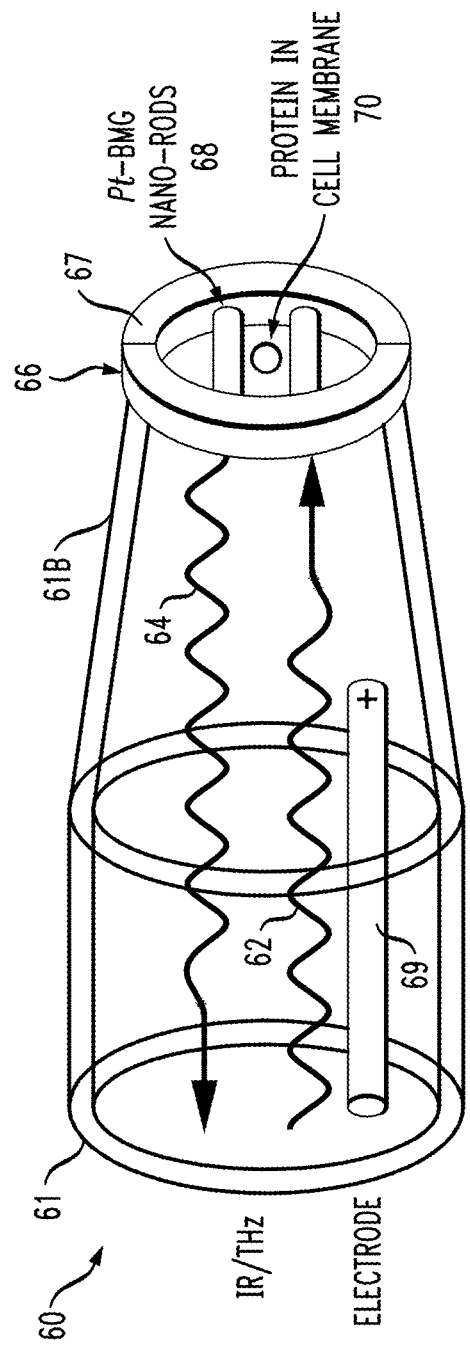
FIG. 1 is a schematic illustration of an exemplary micropipette assembly adapted for facilitating Raman spectroscopy and the patch clamp technique.

Referring to FIG. 1, an exemplary assembly 60 configured for performing the patch clamp technique and obtaining additional chemical information is schematically illustrated. The patch clamp technique may involve the use of a glass micropipette having an open tip to obtain readings relating to the electrical characteristics of a cell membrane. The patch clamp technique has been used, for example, in the analysis of the electrical properties of neurons. The micropipette tip may be positioned in adjoining relation to a cell membrane followed by the application of light suction to form a seal. A gigaseal is formed in some applications of the technique while other variations of the technique require looser seals or no seals between the micropipette and cell membrane. Depending on its diameter, the micropipette tip may be used to collect data from a single ion channel or from multiple ion channels at the same time. The assembly 60 disclosed herein includes a micropipette 61 having a SERS-facilitating assembly 66 incorporated at the tip. The assembly 66 includes an annular base 67 and Pt-BMG nano-rods 68 or other bio-compatible SERS-facilitating structures. The nano-rods in the exemplary structure are in a plane that extends perpendicularly with respect to the longitudinal axis of the micropipette 61. The Pt-BMG nano-rods have diameters less than two hundred fifty nanometers (250 nm) and are positioned within five and two hundred fifty nanometers (5-250 nm) of each other to facilitate SERS. The annular base 67 of the assembly 66 contacts the cell wall to be probed and can be made from glass, as described further below. The diameter of the annular base 67 may be about the same as that of the opening at the tip end 61B of the micropipette. The annular base 67 has an inner diameter between about 5-50 µm, typically several (2-5 microns) larger than the outer diameter of the pipette, for a close fitting. Diameters in this range may be used for obtaining data relating to multiple membrane ion channels. Suction is employed to provide a seal to isolate a cell membrane patch, possibly trapping transmembrane proteins within the SERS-facilitating nano-rod grid. Proteins interacting with the grid are subjected to monochromatic light 62 of a selected frequency, resulting in enhanced Raman scattering. The scattered light 64 is collected for spectroscopic analysis. Concurrently, the patch clamp technique may be employed to monitor ion activity across the membrane through the ion channel(s). When an electrical event is detected (ion channel activation), the corresponding Raman spectra may be used to identify proteins that interact with the grid.

An electrode 69 is located within an electrolyte solution that fills the micropipette and enables the recording of current flow. The electrode 69 may be electrically connected to a differential amplifier (not shown) to enhance current detection. Ions flow through the ion channels and produce a voltage or current pulse and that signal is amplified by the amplifier (relative to the ex-cellular fluid grounding). As known in the art, the patch clamp technique involves electrically isolating a patch of a cell membrane from an external solution and recording current flowing into the patch. The assembly 60 provided herein allows both electrical and chemical data to be obtained by incorporating the SERS-facilitating assembly at the tip end of a micropipette.

Figure 2C:
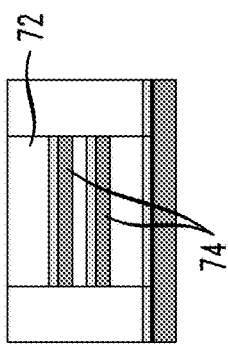
FIGS. 2A-2H include a flow diagram showing fabrication of an exemplary nanowire assembly for facilitating Raman spectroscopy of using a micropipette.
Figure 2F:
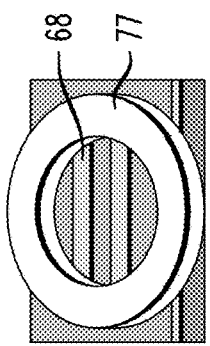
Figure 2B:
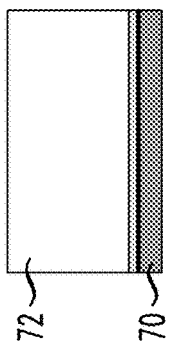
Figure 2E:
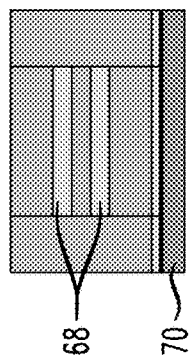
Figure 2H:
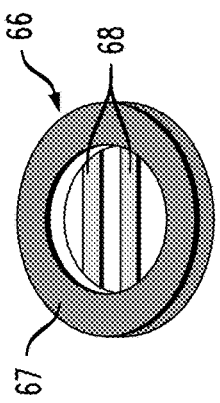
Figure 2A:
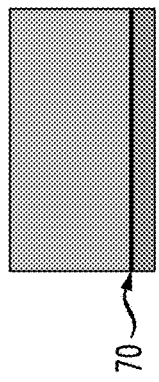
Figure 2D:
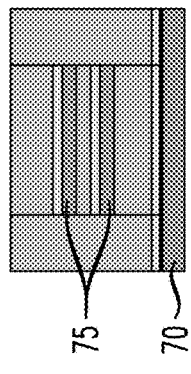
Figure 2G:
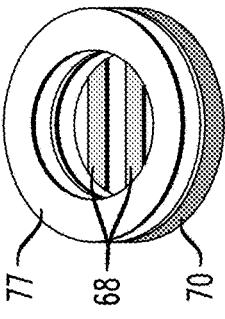

FIGS. 2A-2H schematically illustrate a process for fabricating an exemplary SERS-facilitating assembly for use in conjunction with a micropipette. A glass substrate 70, for example borosilicate glass, is coated with a layer 72 of photoresist as shown in FIGS. 2A and 2B. Referring to FIG. 2C, the photoresist is patterned to include longitudinal openings 74 having dimensions corresponding to the nano-rods to be formed in the finished assembly 66. The spacing between longitudinal openings will correspond to the spacing between nano-rods in the assembly 66. While only two parallel openings in the photoresist are shown for purposes of illustration, it will be appreciated that multiple openings or groups of openings may be formed to provide closely packed group(s) of nano-rods, some of which may or may not be parallel to the other group(s) of openings. The pattern formed in the photoresist layer 72 is transferred to the glass substrate 70 using a reactive ion etch (RIE). Grooves 75 in the substrate 70 corresponding to the openings 74 in the photoresist are thereby formed, as shown in FIG. 2D. Nano-rods 68 are formed within the grooves 75 in the substrate 70, as schematically illustrated in FIG. 2E. In an exemplary process, after the resist is patterned, the image of the resist is transferred into the glass substrates 70 by using a reactive ion etch (RIE) process, such as using $CHF_3.O_2$ etch gases to form the grooves in the glass substrates. The RIE process allows the etch profile to be controlled by varying ME conditions, such as pressure and flow rate, such to determine if the nano-rod cross sections are to be round, square, or trapezoidal. Once the grooves are transferred to the glass substrates, the metal is filled into the grooves to form the SERS structures. In the case of Pt bulk-metallic-glass (Pt-BMG), the material is hot pressed into the grooves at 250° C. For other high melt materials like Pt, Au, Ag, and $TiO_2$, the materials are either evaporated or ion sputtered into the grooves and is followed by a chemical-mechanical polish (CMP) to remove the materials in the field area (between the grooves), leaving the deposited materials only in the grooves. In summary, resist is removed after RIE etch pattern transfer onto the glass carrier, metals are filled into the grooves using hot press (Pt-BMG) or sputtering (e.g. Pt, Au, Ag), followed by a grind/polish to remove the field area (between the grooves)) A second photoresist layer 77 is deposited and patterned into a circular configuration corresponding to the desired inner and outer diameters of the annular base/frame 67 of the SERS-facilitating assembly 66. FIG. 2F shows the patterned resist layer. The resulting structure is subjected to a selective etch that removes the unprotected portion of the glass substrate 70. A structure as schematically illustrated in FIG. 2G is accordingly obtained. The nano-rods 68 are imbedded in the annular base as shown in FIG. 2H and are attached to the now-annular glass substrate 70 only at their end portions. The photoresist layer 77 is stripped to obtain the assembly shown in FIG. 2H to obtain the SERS-facilitating assembly 66 to be attached to a micropipette. The size of the opening in the assembly 66 corresponds closely to the size (diameter) of the tip opening of the micropipette with which it is intended to be used in some embodiments. Sufficient open space is provided within the assembly to allow suction to be applied to a cell membrane through the micropipette while enabling SERS and single molecule detection.

Figure 6A:
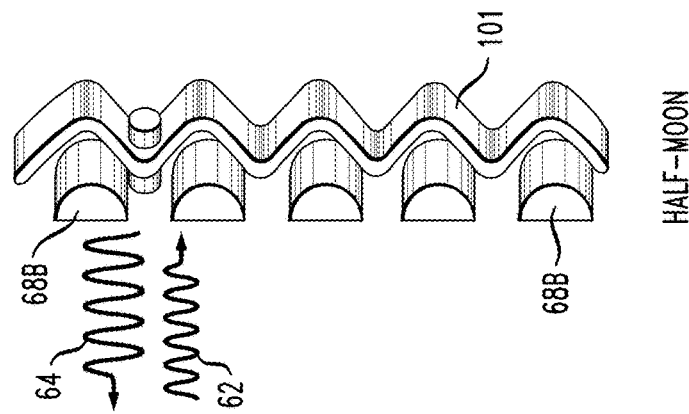
Figure 6B:
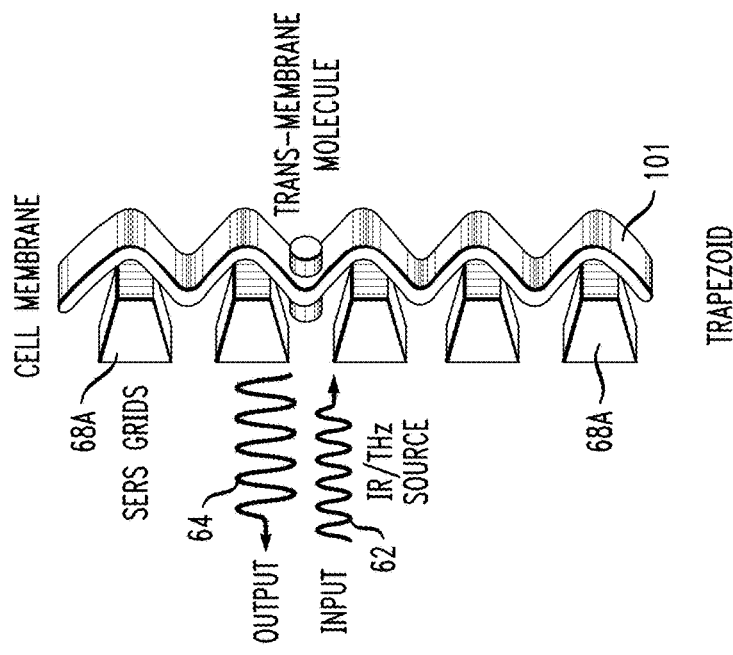
Figure 6C:
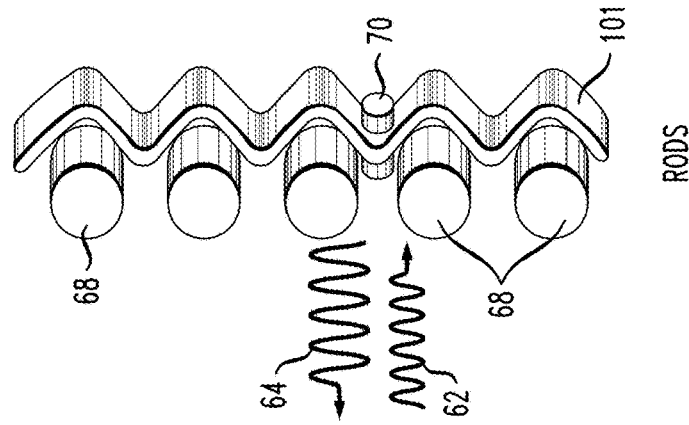

FIGS. 3A-3C illustrate the process of attaching the SERS-facilitating assembly 66 to a micropipette 61. The micropipette may include a cylindrical body portion 61A and a tip portion 61B. Glass micropipettes having tip inner diameters ranging from less than a micron to tens of microns are commercially available. The micropipette and the assembly 66 are positioned such that their longitudinal axes are aligned and the annular base 67 is in opposing relation to the annular rim 63 at the tip end of the micropipette. The annular base 67 is moved into contact with the rim 63 and attached thereto. Laser welding may be employed to effect such attachment. In embodiments where the nano-rods 68 are formed within grooves on a glass substrate as described above, the side of the annular base 67 lacking the grooves and nano-rods forms the exposed tip of the assembled structure shown in FIG. 3C while the surface including grooves and nano-rods contacts the rim 63 of the micropipette. The annular surface of the assembly that contacts a cell is configured to facilitate good contact with the cell membrane and a tight seal upon the application of suction during performance of the patch clamp technique. The nano-rods 68 extending across the annular base 67 do not materially impair the ability to apply suction as the opening defined by the annular base remains sufficiently unobstructed. The nano-rods are configured to facilitate SERS with respect to one or more targeted molecules while allowing electrophysiological data relating to the cell ion channel(s) to be obtained. The structure can accordingly be employed to obtain both electrophysiological data using the patch clamp technique and chemical data using Raman (including terahertz-Raman) spectroscopy. Either side of the assembly 66 can be in contact with cell, but preferably the side with nano-rod edges (if present) facing the laser. If the nano-rods have round cross sections, as shown in FIG. 6A, there is no preference. In embodiment wherein the nano-rods have half-moon cross sections as shown in FIG. 6C, the flat side should face the laser, as the sharp edges are where SERS enhancement is highest. In the case of FIG. 6B, wherein the assembly includes nano-rods having trapezoidal cross sections, the larger side facing the laser will provide slightly better enhancement because of the smaller distance between them.

An alternative embodiment of a SERS-facilitating assembly 90 is schematically illustrated in FIGS. 4A and 4B. This assembly is used when the nano-rods are too long to stretch across the ring (e.g. annular base portion 67 shown in FIG. 3B) with sufficient stability. The nano-rods 94 are assembled using relatively smaller frames instead, with a larger ring 95 attached to the micropipette 61 for stability and rigidity. Referring to FIG. 4B, the tip of a micropipette 61 as shown in FIG. 3A would be inserted into the ring 95 from the left of the figure. The assembly 90 can be formed using techniques similar to those used for fabricating the SERS-facilitating assembly 66 described above with respect to FIGS. 2A-2G. The patterning of the photoresist layer(s) employed during fabrication would, of course, be different from those described above to obtain a different pattern of nano-rods. The assembly 90 includes a circular glass holder 92 having four rectangular openings 93 therein. The ring 95, which may also be glass, and the glass holder 92 form a shallow recess sized to accommodate the tip end of a micropipette and facilitate alignment therewith. The tip end would contact the periphery of the glass holder 92 in some embodiments and could also contact the ring 95. The ring further provides an annular surface that is used to form a seal with a cell membrane when used for the patch clamp technique. The diameter of the glass holder 92 matches the outside tip diameter of some micropipettes. Larger diameter holders can be employed for larger micropipettes used to form patches including larger numbers of cell ion channels. Nano-rods 94 are attached to the holder 92 and extend across each opening 93. The nano-rods extend horizontally across one of the openings 93 and vertically across the other three openings 93 in the exemplary embodiment. It will be appreciated that the nano-rods may have different orientations in other embodiments. The composition, size and spacing of the nano-rods are selected to facilitate SERS with respect to the molecules 96 (e.g. proteins, enzymes) to be detected. Pt-BMG nano-rods having diameters between twenty and five hundred nanometers, (250 nm nano-rod diameter being typical) and positioned within five and two hundred fifty nanometers (5-250 nm) of each other facilitate SERS and single molecule detection using SERS. The nano-rods within one or more openings 93 may have the same diameters and spacing as those within other openings. Alternatively, the diameters and/or spacing of the nano-rods may be different in one or more of the openings from those in other openings. The compositions of the nano-rods and/or coatings thereon may or may not be the same in all of the openings. The sizes of the openings 93 and the spaces between nano-rods 94 allow sufficient fluid flow such that, when the assembly 90 is secured to the tip end of a micropipette and positioned adjacent to a cell, the patch clamp technique can be employed to obtain electrophysiological data while chemical information relating to individual molecules 96, enhanced by the SERS grid, is reflected back and collected.

The nano-rods employed in the embodiments discussed above have sizes and shapes chosen to facilitate SERS. Bulk metallic glass (BMG) nano-rods may be employed, such as platinum-based BMG nano-rods having the composition $Pt_{57.5}Cu_{14.7}Ni_{5.3}P_{22.5}$. The Pt-BMG nano-rods can be coated with gold or silver nanoparticles to provide additional signal enhancement, though such coatings are not required as Pt-BMG nano-rods facilitate SERS without any coatings for at least some molecules such as glucose. Nano-rods formed from other materials, such as zinc oxide (ZnO), do not effectively facilitate SERS and accordingly should be coated with a metal such as silver. The SERS-facilitating assembly at the distal end of the micropipette may be comprised of materials other than Pt-BMG and structures other than nano-rods that facilitate SERS. Gold and silver surfaces including bio-compatible materials are among the possible options. An analyte molecule 96 in the vicinity of an effective plasmonic surface is characterized by increased absorption of the emitted light and an increased Raman signal.

Figure 5:
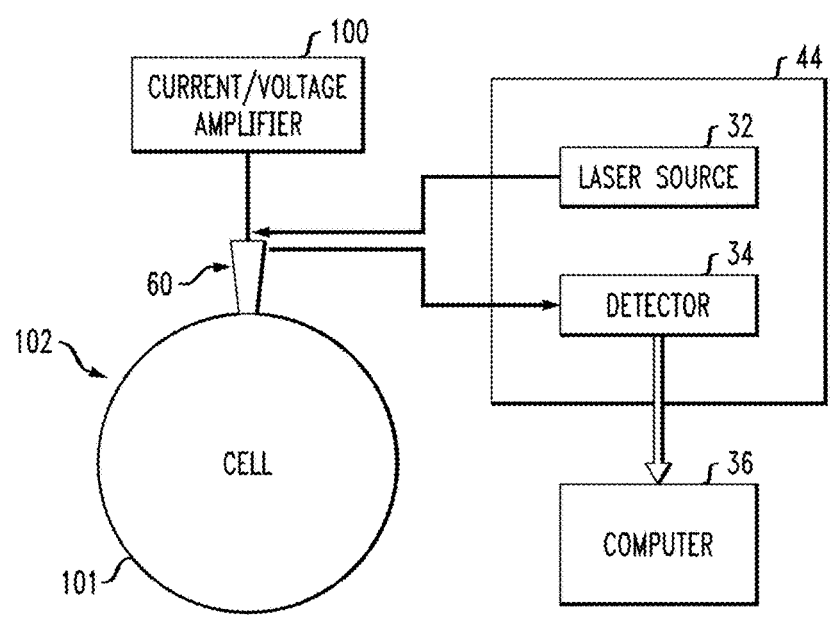
FIG. 5 is a schematic diagram of a system for obtaining spectroscopic and electrical data using a micropipette including a SERS-facilitating structure, and FIGS. 6A-6C includes schematic illustrations showing SERS-facilitating grids having different cross sections in adjoining relation to a cell membrane.

FIG. 5 shows an exemplary system including the exemplary assembly 60 and operatively associated devices. A laser source 32 is optically aligned with the SERS-facilitating assembly. In some embodiments, the laser source is a distributed feedback laser (DFB) such as a quantum cascade laser (QCL). The laser source for performing SERS may, for example, be employed for providing 532 nm (green), 632 nm (red), 785 nm (NIR), 1032 nm, or other suitable wavelengths. Terahertz (THz) radiation can alternatively be emitted using solid state lasers. Scattered light is collected by a detector 34 such as a spectroscope. A computer 36 having an optional display is operatively associated with the detector 34 and may be used for controlling the detector and laser source as well as for electronic storage of operational parameters and data. In this exemplary use, the tip of the assembly 60, which includes the SERS-facilitating assembly 66, is moved into contact with the membrane of a cell 102. A seal is formed with the membrane which allows the subsequent application of suction. A selected variation of the patch clamp technique is performed to obtain electrical data relating to the cell membrane ion channels. A current/voltage amplifier 100 is operatively associated with the electrode 69 (see FIG. 1) within an electrolyte solution and facilitates detection of the small currents and changes in such currents associated with performance of the patch clamp technique. Chemical sensing can be conducted by actuating the laser source and directing light having a selected wavelength through the micropipette body and onto the SERS-facilitating assembly adjoining the cell membrane 101. Scattered light is collected by the detector 34 and analyzed. Chemical information relating to molecules adjoining the SERS-facilitating assembly can be obtained by spectroscopic analysis of the scattered light.

FIGS. 6A-6C schematically illustrate portions of various SERS-facilitating assemblies in adjoining relation to cell membranes 101. The embodiment of FIG. 6A includes an array of parallel cylindrical nano-rods 68. Scattered light 64 allows the spectroscopic analysis of the molecule 70 within the nano-rod grid. FIGS. 6B and 6C show SERS-facilitating assemblies including nano-rods having trapezoidal and hemispherical cross-sections, respectively. The nano-rods 68A and 68B include sharp edge portions running along their lengths that further facilitate SERS. It will be appreciated that nano-rods having other configurations that prove effective for SERS can alternatively be employed. The nano-rods 68, 68A and 68B comprise $Pt_{57.5}Cu_{14.7}Ni_{5.3}P_{22.5}$ in some embodiments. Such nano-rods may include gold or silver nanodots.

Given the discussion thus far, an exemplary method includes using the same device to perform the patch clamp technique for obtaining electrophysiological data relating to ion channels as well as SERS for obtaining chemical data. Such a method includes obtaining a micropipette 61 including an open tip portion configured for facilitating surface enhanced Raman spectroscopy and positioning the tip portion of the micropipette in adjoining relation to a cell membrane 101. An electrolyte solution is introduced within the micropipette. Suction is applied through the micropipette while the tip portion is in adjoining relation to the cell membrane. The tip portion may or may not contact the cell membrane prior to the application of suction. The method further includes conducting a patch clamp technique using the micropipette to obtain electrophysiological data with respect to the cell membrane. Monochromatic light 62 having a selected wavelength is directed towards the tip portion of the micropipette, which may include molecules such as proteins or enzymes interacting with the tip portion. Surface enhanced Raman scattered light 64 generated at the tip portion of the micropipette is conveyed to a detector 34 for spectral analysis of the scattered light. Molecule(s) 70 interacting with the tip portion can accordingly be identified. In some embodiments, the tip portion includes nano-rods 68 (or 68A, 68B) configured to interact with one or more molecules of interest and thereby facilitate SERS. The nano-rods can be attached to an annular base portion 67 as schematically shown in FIG. 3C. In some embodiments, the nano-rods are Pt-BMG nano-rods. Nano-rods coated with silver or gold nanodots can be employed to facilitate SERS.

An exemplary assembly for performing the patch clamp technique as well as facilitating chemical sensing includes a micropipette having a body portion and a tip portion. FIGS. 1 and 3C schematically illustrate exemplary micropipettes. A SERS-facilitating assembly 66 is attached to the tip portion of the micropipette and includes an annular surface for providing sealing contact with a cell membrane during performance of the patch clamp technique. The SERS-facilitating assembly is configured for interacting with selected molecule(s) and thereby enhancing Raman scattering while allowing fluid passage therethrough. Suction can accordingly be provided by the micropipette despite the presence of SERS-facilitating structures such as nano-rods. In some embodiments, the SERS-facilitating structures include Pt-BMG nano-rods that are attached to an annular glass base. The exemplary assembly can further include an electrode 69. FIG. 6 schematically illustrates an electrode 69 that is employed within an electrolyte solution during performance of the patch clamp technique. A laser source 32 may further be provided for directing monochromatic light (infrared or terahertz) towards the SERS-facilitating assembly. The scattered light 64 is processed by a detector 34 such as a spectrometer. In some embodiments, electrical data such as voltage clamp recordings and data relating to cell chemistry are obtained simultaneously.

A fabrication method is further provided to produce a device that can be employed for obtaining spectroscopic information relating to molecules of interest as well as electrophysiological data. The method includes obtaining a micropipette 61 having an open end portion, obtaining a SERS-facilitating assembly including a base, an opening extending through the base, and a plurality of nano-rods attached to the base, the nano-rods extending across the opening, and attaching the SERS-facilitating assembly to the open end portion of the micropipette. FIGS. 3A-3C schematically illustrate an embodiment of the fabrication method. As further shown in FIGS. 2A-2D, the SERS-facilitating assembly can be obtained by forming grooves 75 in a substrate 70, forming the nano-rods 68 within the grooves, and forming the base 67 from the substrate. The base includes an annular surface for contacting a cell membrane. The micropipette 61 is attached to an opposite side of the base. The annular surface for contacting the cell membrane has an inner diameter of about five to fifty microns in some embodiments. The base is sized for attachment to the tip of a micropipette and has an annular surface for contacting the cell membrane and forming a seal therewith.

In addition to the infrared (IR) Raman spectrum for chemical (bond) analysis, the spectrum also extends into the terahertz region for macromolecule (very large proteins and enzymes) structure detection, such as protein structural vibration in membrane. The devices and techniques disclosed herein provide a viable method to effectively excite and detect such motion (in-vivo in membrane). Proteins and enzymes (such as lysozymes and ribosomes) are very large molecules and can have their crystal structure determined by x-ray crystallography. Terahertz-Raman processing as disclosed herein allows the determination of, for example, the link between their DNA/amino sequence and their enzymatic functionality. In a normal terahertz analysis, the wavelength is such that terahertz cannot focus on to a single molecule. A normal SERS Raman can detect a single molecule chemically (through bond, or optical mode)) but not its structure. Terahertz-Raman involves the use of very high resolution Raman to obtain terahertz information (molecular structure through its acoustic signature). Terahertz-Raman with SERS as provided herein allows single molecule terahertz information (large molecular structural information) to be detected and the linking of such information to their enzymatic function(s).

The illustrations of embodiments described herein are intended to provide a general understanding of the various embodiments, and they are not intended to serve as a complete description of all the elements and features of apparatus and systems that might make use of the assemblies and techniques described herein. Many other embodiments will become apparent to those skilled in the art given the teachings herein; other embodiments are utilized and derived therefrom, such that structural and logical substitutions and changes can be made without departing from the scope of this disclosure. It should also be noted that, in some alternative implementations, some of the steps of the exemplary methods may occur out of the order noted in the specification and/or figures. For example, two steps shown in succession may, in fact, be executed substantially concurrently, or certain steps may sometimes be executed in the reverse order, depending upon the functionality involved. The drawings are also merely representational and are not drawn to scale. Accordingly, the specification and drawings are to be regarded in an illustrative rather than a restrictive sense.

Embodiments are referred to herein, individually and/or collectively, by the term "embodiment" merely for convenience and without intending to limit the scope of this application to any single embodiment or inventive concept if more than one is, in fact, shown. Thus, although specific embodiments have been illustrated and described herein, it should be understood that an arrangement achieving the same purpose can be substituted for the specific embodiment(s) shown; that is, this disclosure is intended to cover any and all adaptations or variations of various embodiments. Combinations of the above embodiments, and other embodiments not specifically described herein, will become apparent to those of skill in the art given the teachings herein.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. Terms such as "above" and "below" are used to indicate relative positioning of elements or structures to each other as opposed to relative elevation.

The corresponding structures, materials, acts, and equivalents of any means or step-plus-function elements in the claims below are intended to include any structure, material, or act for performing the function in combination with other claimed elements as specifically claimed. The description of the various embodiments has been presented for purposes of illustration and description, but is not intended to be exhaustive or limited to the forms disclosed. Many modifications and variations will be apparent to those of ordinary skill in the art without departing from the scope and spirit thereof. The embodiments were chosen and described in order to best explain principles and practical applications, and to enable others of ordinary skill in the art to understand the various embodiments with various modifications as are suited to the particular use contemplated.

The abstract is provided to comply with 37 C.F.R. § 1.72(b), which requires an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the appended claims reflect, the claimed subject matter may lie in less than all features of a single embodiment. Thus the following claims are hereby incorporated into the Detailed Description, with each claim standing on its own as separately claimed subject matter.

Given the teachings provided herein, one of ordinary skill in the art will be able to contemplate other implementations and applications of the techniques and disclosed embodiments. Although illustrative embodiments have been described herein with reference to the accompanying drawings, it is to be understood that illustrative embodiments are not limited to those precise embodiments, and that various other changes and modifications are made therein by one skilled in the art without departing from the scope of the appended claims.

What is claimed is:

1. A fabrication method comprising:
    obtaining a micropipette having an open end portion;
    obtaining a SERS-facilitating assembly including a base, an opening extending through the base, and a plurality of nano-rods attached to the base, the nano-rods extending across the opening, the SERS-facilitating assembly being configured for interacting with one or more selected molecules and enhancing Raman scattering with respect to the one or more selected molecules while allowing fluid passage therethrough; and
    attaching the base of the SERS-facilitating assembly to the open end portion of the micropipette, enabling fluid passage through the SERS-facilitating assembly into the micropipette.

2. The method of claim 1, wherein obtaining the SERS-facilitating assembly further includes:
    forming grooves in a substrate,
    forming the nano-rods within the grooves, and
    forming the base from the substrate.

3. The method of claim 2, wherein the nano-rods comprise platinum-based bulk metallic glass, gold, silver, platinum or titanium dioxide.

4. The method of claim 2, wherein forming grooves in the substrate includes:
    applying a first photoresist layer to the substrate;
    patterning the first photoresist layer to include longitudinal openings having dimensions corresponding to the nano-rods; and
    etching the grooves in the substrate corresponding to the longitudinal openings in the first photoresist layer.

5. The method of claim 4, wherein forming the base from the substrate includes:
    depositing a second photoresist layer on the substrate;
    patterning the second photoresist layer into a selected configuration; and
    selectively removing a portion of the substrate.

6. The method of claim 5, wherein the selected configuration is an annular configuration.

7. The method of claim 1, wherein the base has an annular configuration, and attaching the SERS-facilitating assembly to the open end portion of the micropipette further includes attaching the base to a tip portion of the micropipette.

8. The method of claim 7, wherein the base has an inner diameter between five and fifty microns.

9. The method of claim 1, wherein obtaining the SERS-facilitating assembly further includes forming sharp edges on the nano-rods.

10. The method of claim 1, wherein the nano-rods are in a plane extending perpendicularly to a longitudinal axis of the micropipette.

11. The method of claim 10, wherein the nano-rods include cross-sectional configurations including sharp edges.

12. The method of claim 10, wherein the nano-rods have diameters less than two hundred fifty nanometers and are positioned within five and two hundred fifty nanometers of each other.

13. A fabrication method comprising:
   obtaining a micropipette having an open tip portion;
   obtaining a SERS-facilitating assembly including a base, a plurality of openings extending through the base, and a plurality of nano-rods extending across each of the plurality of openings, the SERS-facilitating assembly being configured for interacting with one or more selected molecules and enhancing Raman scattering with respect to the one or more selected molecules while allowing fluid passage therethrough; and
   attaching the base of the SERS-facilitating assembly to the open end portion of the micropipette, enabling fluid passage through the SERS-facilitating assembly into the micropipette.

14. The method of claim 13, wherein the base includes a recess, further including:
   inserting the open tip portion of the micropipette into the recess.

15. The method of claim 13, wherein obtaining the SERS-facilitating assembly further includes:
   patterning a first photoresist layer on the base to include longitudinal openings having dimensions corresponding to the nano-rods; and
   etching the grooves in the substrate corresponding to the longitudinal openings in the first photoresist layer.

16. The method of claim 13, wherein the nano-rods extending across a first of the plurality of openings have a first directional orientation and the nano-rods extending across a second of the plurality of openings have a second directional orientation different from the first directional orientation.

17. The method of claim 13, wherein the nano-rods extending across a first of the plurality of openings have a first diameter and the nano-rods extending across a second of the plurality of openings have a second diameter different from the first diameter.

* * * * *